(12) United States Patent
Yamaguchi et al.

(10) Patent No.: US 8,541,759 B2
(45) Date of Patent: *Sep. 24, 2013

(54) OPTICAL ANALYSIS DEVICE, OPTICAL ANALYSIS METHOD AND COMPUTER PROGRAM FOR OPTICAL ANALYSIS

(75) Inventors: Mitsushiro Yamaguchi, Hachioji (JP); Seiji Kondo, Hachioji (JP); Tetsuya Tanabe, Tokyo (JP); Kunio Hori, Chofu (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/596,280

(22) Filed: Aug. 28, 2012

(65) Prior Publication Data

US 2012/0319009 A1 Dec. 20, 2012

Related U.S. Application Data

(63) Continuation of application No. PCT/JP2011/053483, filed on Feb. 18, 2011.

(30) Foreign Application Priority Data

Mar. 1, 2010 (JP) ................................. 2010-044714

(51) Int. Cl.
*G01J 1/58* (2006.01)
(52) U.S. Cl.
USPC .................................... 250/458.1; 250/459.1
(58) Field of Classification Search
USPC .......................................... 250/458.1, 459.1
See application file for complete search history.

(56) References Cited

U.S. PATENT DOCUMENTS

| 4,251,733 A | 2/1981 | Hirleman, Jr. |
| 6,388,788 B1 | 5/2002 | Harris et al. |

(Continued)

FOREIGN PATENT DOCUMENTS

| JP | 04-337446 A | 11/1992 |
| JP | 2002-507762 A | 3/2002 |

(Continued)

OTHER PUBLICATIONS

Kaneshiro, Masataka, "Single Molecule Detection Using Fluorescence Correlation Spectroscopy", Protein, Nucleic Acid, Enzyme, 1999, pp. 1431-1438, vol. 44 No. 9.

(Continued)

*Primary Examiner* — Christine Sung
(74) *Attorney, Agent, or Firm* — Westerman, Hattori, Daniels & Adrian, LLP

(57) ABSTRACT

The inventive optical analysis technique uses an optical system capable of detecting light from a micro region in a solution, such as an optical system of a confocal microscope or a multiphoton microscope, to detect the light from the light-emitting particle to be observed while moving the position of the micro region in the sample solution (while scanning the inside of the sample solution with the micro region); generates time series light intensity data, computes a characteristic value of the light intensity indicating the presence or absence of the light from a single light-emitting particle in every time section of a predetermined width in the light intensity data; and detects the light-emitting particle crossing the inside of the micro region individually using the characteristic value, thereby enabling the counting of the light-emitting particle(s) or the acquisition of the information on the concentration or number density of the light-emitting particle.

24 Claims, 6 Drawing Sheets

(56) References Cited

U.S. PATENT DOCUMENTS

| | | | |
|---|---|---|---|
| 8,284,484 B2 * | 10/2012 | Hoult et al. | 359/385 |
| 2002/0036775 A1 | 3/2002 | Wolleschensky et al. | |
| 2003/0218746 A1 * | 11/2003 | Sampas | 356/318 |
| 2006/0256338 A1 | 11/2006 | Gratton et al. | |
| 2008/0052009 A1 * | 2/2008 | Chiu et al. | 702/21 |
| 2010/0033718 A1 * | 2/2010 | Tanaami | 356/301 |
| 2010/0177190 A1 * | 7/2010 | Chiang et al. | 348/79 |
| 2010/0202043 A1 * | 8/2010 | Ujike | 359/385 |

FOREIGN PATENT DOCUMENTS

| | | |
|---|---|---|
| JP | 2004-506192 A | 2/2004 |
| JP | 2005-098876 A | 4/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-288161 A | 12/2009 |
| JP | 2011-002415 A | 1/2011 |
| WO | 98/16814 A1 | 4/1998 |
| WO | 99/47963 A1 | 9/1999 |
| WO | 02/12864 A1 | 2/2002 |
| WO | 2006/084283 A2 | 8/2006 |
| WO | 2008/007580 A1 | 1/2008 |
| WO | 2008/080417 A1 | 7/2008 |
| WO | 2009/117033 A2 | 9/2009 |

OTHER PUBLICATIONS

Meyer-Almes, F.J., "Nanoparticle Immunoassays: A new Method for Use in Molecular Diagnostics and High Throughput Pharmaceutical Screening based on Fluorescence Correlation Spectroscopy", Fluorescence Correlation Spectroscopy, 2000, pp. 204-224.

Kato, Noriko et al., "A single molecule analyzer that enable new analysis of DNA and protein interactions", Gene & Medicine, 2002, pp. 271-277, vol. 6 No. 2.

International Search Report of PCT/JP2011/053483, mailing date Mar. 29, 2011.

International Preliminary Examination Report, dated Mar. 30, 2012; issued in PCT/JP2011/053483.

Park et al., "Counting the Number of Fluorophores Labeled in Biomolecules by Observing the Fluorescence-Intensity Transient of a Single Molecule", Bulletin of the Chemical Society of Japan, vol. 78, No. 9, p. 1612-1618, Aug. 30, 2005.

* cited by examiner

FIG. 1A
FIG. 1B
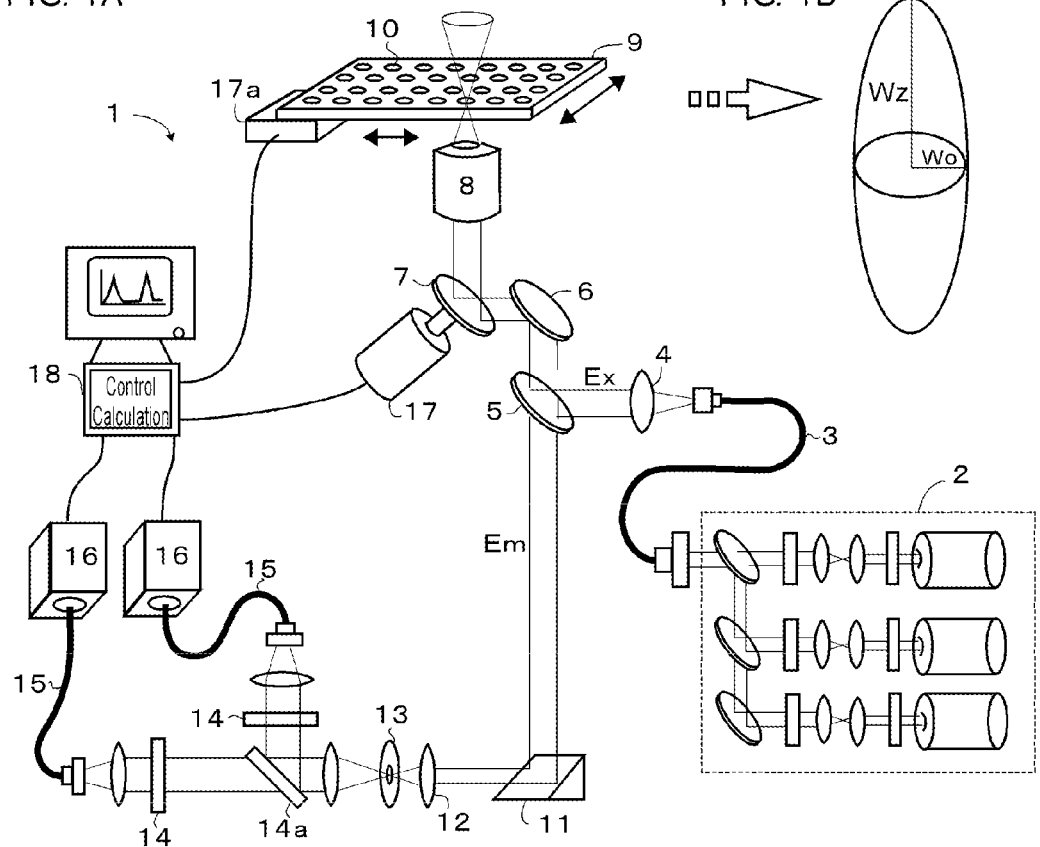
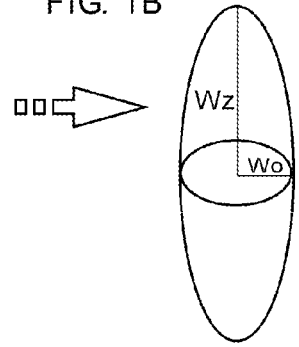
FIG. 1C
FIG. 1D
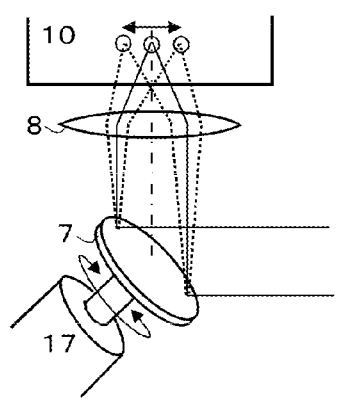
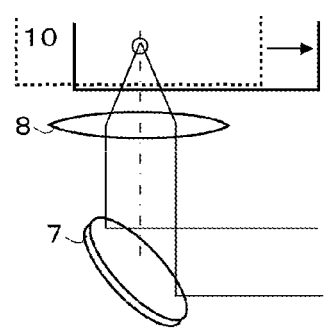

| | Window #30 | Window #31 | Window #32 |
|---|---|---|---|
| Photon Count Total value | 30 | 3 | 17 |
| Photon Count Average value | 1.5 | 0.15 | 0.85 |
| Photon Count SD value | 2.06 | 0.48 | 1.35 |
| Photon Count Variance value | 4.25 | 0.23 | 1.83 |
| Photon Count Entropy | 65.89 | 12.82 | 47.87 |
| Photon Count Maximum value | 5 | 2 | 5 |
| The Number of Particles* | 0.53 | 0.10 | 0.40 |
| | A Particle exists | No particle exists | A Particle exists |

\* Computed from Autocorrelation function value.

High Concentration (e. g. ~ 1nM)

Low Concentration (e. g. ~ 1pM)

OPTICAL ANALYSIS DEVICE, OPTICAL ANALYSIS METHOD AND COMPUTER PROGRAM FOR OPTICAL ANALYSIS

TECHNICAL FIELD

This invention relates to an optical analysis device, an optical analysis method and a computer program for them, which detects light from an atom, a molecule or an aggregate (Hereafter, these are called a "particle".) dispersed or dissolved in a solution, for analyzing the conditions of the particles in the solution, and more specifically, relates to an optical analysis device, an optical analysis method and a computer program for optical analysis, capable of acquiring useful information in an analysis of conditions (interaction, binding or dissociating condition, etc.) of various particles, such as biological molecules, for example, protein, peptide, nucleic acid, lipid, sugar chain, amino acid or these aggregate, particulate objects, e.g. viruses and cells, or non-biological particles by using an optical system, such as the optical system of a confocal microscope or a multiphoton microscope, which can detect light from a micro region in a solution.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of intermolecular interaction, binding or dissociating reaction of biological molecules, etc. by means of such a faint light measurement technique. For example, in Fluorescence Correlation Spectroscopy (FCS, see e.g. patent documents 1 and 2 and non-patent documents 1-3), by means of the optical system of a laser confocal microscope and a photon counting technique, there is performed the measurement of fluorescence intensity of fluorescence molecules or fluorescently labeled molecules (fluorescent molecules, etc.), entering into and exiting out of a micro region in a sample solution (the focal region to which the laser light of the microscope is condensed, called a "confocal volume"), and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 3) or Photon Counting Histogram (PCH, e.g. patent document 4), there is generated a histogram of fluorescence intensity of fluorescent molecules, etc., entering into and exiting out of a confocal volume, measured similarly to FCS, and the average value of the characteristic brightness of the fluorescent molecules, etc. and the average number of molecules dwelling in the confocal volume are calculated by fitting a statistical model formula to the distribution of the histogram, so that, based on the information thereof, the structure or size change, binding or dissociative conditions or dispersion and aggregation conditions of molecules will be estimated. Moreover, in patent documents 5 and 6, there are proposed methods of detecting fluorescent substances based on a time progress of a fluorescence signal of a sample solution measured using the optical system of a confocal microscope. Patent document 7 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the method employing the fluorescent light measurement technique of a micro region using the optical system of a confocal microscope and a photon counting technique, such as FCS and FIDA, a sample amount required for the measurement may be extremely small (an amount used in one measurement is at most several tens of µL), and its concentration is extremely low as compared with the prior art, and the measuring time is also shortened extremely (In one measurement, measurements for time of order of seconds are repeated several times.). Thus, those techniques are expected to be a strong tool enabling an experiment or a test at low cost and/or quickly in comparison with conventional biochemical methods, especially in conducting an analysis of rare or expensive samples often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent No. 4023523
Patent document 4: WO 2008-080417
Patent document 5: Japanese Patent laid-open publication No. 2007-20565
Patent document 6: Japanese Patent laid-open publication No. 2008-116440
Patent document 7: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.

SUMMARY OF INVENTION

Technical Problem

In the above-mentioned optical analysis techniques, such as FCS, FIDA and PCH, briefly speaking, the magnitude of time fluctuation of measured fluorescence intensity is computed by a statistical procedure, and then various characteristics of fluorescent molecules, etc., entering in and exiting out of a micro region in a sample solution, are determined based on the magnitude of the fluctuation. Thus, in order to obtain a significant result in the above-mentioned optical analysis technique, it is preferable to prepare the concentration or number density of fluorescent molecules, etc. used as the observation objects in the sample solution so that fluorescent molecules, etc. of the number enabling a statistical process will enter in and exit from a micro region in one measuring term of a length of order of seconds in an equilibrium, preferably so that about one fluorescent molecule, etc. will be always exist in the micro region (Typically, since the volume of a confocal volume is about 1 fL, it is preferable that the concentration of fluorescent molecules, etc. is about 1 nM or more.). In the other words, when the concentration or number density of particles to be observed in a sample solution is much lower than the level enabling a statistical process (for example, much lower than 1 nM), there would occur a condition where an object to be observed rarely enters into the micro region in the measuring term, and accordingly, the measuring result of fluorescence intensity would include a long period of a condition in which no objects to be observed exist at all in the micro region and also the amount of observation of significant fluorescence intensity would decrease, and thus no significant or accurate analysis result could be expected in the optical analysis technique based on the statistical fluctuation of the fluorescence intensity as described above.

In the method of detecting fluorescent substances using the optical system of a confocal microscope described in patent documents 5 and 6, without performing the statistical process of the fluorescence intensity fluctuation as described above, the presence or absence of a fluorescent molecule, etc. to be observed in a sample can be determined from the presence or absence of generation of a fluorescence signal having a significant intensity in the measuring term over several seconds and it is disclosed that a correlation between the frequency of fluorescence signals having significant intensity and the number of the fluorescent molecules, etc. in a sample is obtained. In particular, in patent document 6, it is suggested that the generation of a random flow agitating the inside of a sample solution improves the detection sensitivity. However, even in those methods, the existences of fluorescent molecules, etc. entering into a micro region at random by diffusion or a random flow is simply detected, where the behavior of a particle of the fluorescent molecules, etc. in the micro region cannot be grasped, and therefore, for instance, the counting of particles or the quantitative computing of the concentration or number density of particles have not been achieved. Moreover, the technique described in patent document 7 is to detect individual existences of fluorescent fine particles in the flow in a flow cytometer or fluorescent fine particles fixed on a substrate, not a technique for detecting particles, such as molecules and colloids, being dissolved or dispersed in a normal condition in a sample solution, i.e. particles moving at random in a sample solution, and thus, it has not been achieved to quantitatively compute out the concentration or number density of particles dissolved or dispersed in a sample solution. Further, since the technique of patent document 7 includes processes, such as the measurement in a flow cytometer or the treatment of fixing fluorescence particles on a substrate, the sample amount necessary for the test increases substantially as compared with the cases of the optical analysis techniques, such as FCS, FIDA and PCH, and complicated and advanced operational techniques may be requested to a person conducting the test.

Thus, one of objects of the present invention is to provide a novel optical analysis technique which does not include statistical procedures as performed in optical analysis techniques, such as FCS, FIDA and PCH, so that the detection of a condition or a characteristic of a particle to be observed is enabled in a sample solution containing the particle to be observed at a concentration or number density lower than the level treatable in optical analysis techniques, such as FCS, FIDA and PCH.

In addition, another object of the present invention is to provide an optical analysis device, method or computer program for it, realizing a new optical analysis technique as described above, wherein a measurement can be done with a small sample amount (for example, several tens of µL level) in a short measuring term similarly to optical analysis techniques, such as FCS, FIDA and PCH, and also characteristics, such as a concentration or a number density, of a particle to be observed can be quantitatively determined.

Solution to Problem

Generally, in the present invention, there is proposed a novel type of an optical analysis technique for detecting light from a particle which emits light (hereafter, called a "light-emitting particle"), and is dispersed and moving at random in a sample solution, by means of an optical system which can detect the light from a micro region in a solution, such as an optical system of a confocal microscope or a multiphoton microscope, which technique detects the light from the micro region, i.e., a light detection region, while moving the position of the micro region in the sample solution (i.e., while scanning the inside of the sample solution with the micro region), thereby detecting individually the light-emitting particle crossing the inside of the micro region and enabling the counting of the light-emitting particles and the acquisition of the information on the concentration or number density of the light-emitting particle in the sample solution.

According to the present invention, as one aspect, there is provided an optical analysis device which detects light from a light-emitting particle dispersed and moving at random in a sample solution by using an optical system of a confocal microscope or a multiphoton microscope, characterized in that the device comprises: a light detection region moving mechanism which moves a position of a light detection region of the optical system in the sample solution; a light detector which detects light from the light detection region; and a signal processor which generates time series light intensity data of the light from the light detection region detected with the light detector during moving the position of the light detection region in the sample solution, and then detects individually a light signal from each light-emitting particle in the time series light intensity data; wherein the signal processor computes a characteristic value of a light intensity indicating a presence or an absence of light from a single light-emitting particle in every time section of a predetermined width in the time series light intensity data, and detects individually a light signal from each light-emitting particle, using the characteristic value. In this structure, "a light-emitting particle dispersed and moving at random in a sample solution" is a particle, such as an atom, a molecule or an aggregate of these, emitting light and being dispersed or dissolved in a sample solution, and it may be an arbitrary particulate matter making the Brownian motion freely in a solution without being fixed on a substrate, etc. This light-emitting particle is typically a fluorescent particle, but may be a particle which emits light by phosphorescence, chemiluminescence, bioluminescence, light scattering, etc. The "light detection region" of the optical system of a confocal microscope or a multiphoton microscope is the micro region where light is detected in those microscopes, which region corresponds to the region to which illumination light is condensed when the illumination light is given from an objective (This region is determined in accordance with the spatial relationship of an objective and a pinhole especially in a confocal microscope. For a light-emitting particle which emits light without illumination light, for example, a particle which emits light according to chemiluminescence or a bioluminescence, no illumination light is required in a microscope.). In this regard, in this specification, "a light signal" means "a signal indicating light".

As understood from the above, in the basic structure of the inventive device, first, the detection of light is sequentially performed while the position of a light detection region is moved in a sample solution, namely, while the inside of the sample solution is scanned with the light detection region. Then, when the moving light detection region includes a randomly moving light-emitting particle, the light from the light-emitting particle is detected by the light detector, and thus, by catching this light, the existence of one light-emitting particle will be detected. In this connection, more in details, in the signals outputted in time series from the light detector, i.e., in the light intensity data, the value of the output signal of the light detector in a time section where the light from a single light-emitting particle has arrived at the light detector varies in a pulse form, having a characteristic different from the value in a time section where no light from a light-emitting particle has arrived and only noise has been generated. Thus, the signal processor of the inventive device is designed to generate time series light intensity data from signals sequentially detected by the light detector; computes out a characteristic value of light intensity indicating the presence or absence of the light from a single light-emitting particle for every time section of a predetermined width in the time series light intensity data and detects individually a light signal from each light-emitting particle using the characteristic value.

As the characteristic value, there may be employed an arbitrary value whose magnitude in a time section of a predetermined width in which a light from a single light-emitting particle exists becomes larger than the magnitude in a time section of a predetermined width in which no light from a single light-emitting particle exists. In that case, it is judged that a light signal from a light-emitting particle exists in the time section of the predetermined width when the characteristic value of light intensity is larger than a predetermined threshold value. For example, such a characteristic value may be either of the integrated value of the light intensity, the center value of the light intensity, the average value of the light intensity, the standard deviation of the light intensity, the variance of the light intensity, the entropy of the light intensity, the maximum value of the light intensity and the number of particles computed from the value of an autocorrelation function of the light intensity with the correlation time being set to 0, in the time section of the predetermined width. In this regard, typically, the light detector detects the light from the light detection region by the photon counting, and therefore, in that case, the time series light intensity data is time series photon count data. Thus, the characteristic value of light intensity may be a value selected from selected from a group of a total value of photon counts, a center value of photon counts, an average value of photon counts, a standard deviation of photon counts, a variance of photon counts, an entropy of photon counts, a maximum value of photon counts and the number of particles computed from an autocorrelation function value of photon counts with a correlation time being set to 0, in the time section of the predetermined width.

Also, in the case of the way of detecting a signal of a light-emitting particle using a characteristic value for every time section of a predetermined width as described above, if the predetermined width is shorter than a time width required for an interval from a time in which one light-emitting particle enters into the light detection region to a time the light-emitting particle exits from the light detection region, the light of one light-emitting particle would be detected over two or more time sections; while the predetermined width is so long that the arrival times of the light of a plurality of light-emitting particles are covered, the information on two or more light-emitting particles would be included in one time section, and in either of the cases, the relation that one light-emitting particle corresponds to one time section would not be established, and consequently, the signal processing for detecting individually a light signal from each light-emitting particle would become complicated. Then, preferably, the predetermined width is set to be substantially longer than a time width required for an interval from a time of one light-emitting particle's entering into the light detection region to a time of its exiting therefrom, and also substantially shorter than a time width from a time of one light-emitting particle's entering into the light detection region to a time of a different light-emitting particle's entering into the light detection region. In the other words, the lower limit of the predetermined width of the time section is set to be substantially longer than the time width of the light signal of one light-emitting particle and its upper limit is set such that the number of light-emitting particles covered in each time section will be substantially not more than one particle. In this regard, in the expression described above, "substantially longer than a time width required for an interval from a time of one light-emitting particle's entering into the light detection region to a time of its exiting therefrom" or "substantially longer than the time width of the light signal of one light-emitting particle" means that the predetermined width is set to be longer than the time widths of the light signals of most light-emitting particles, namely, the existence of a light signal of a light-emitting particle having a time width longer than the predetermined width is allowed within the range of error. Also, "substantially shorter than a time width from a time of one light-emitting particle's entering into the light detection region to a time of a different light-emitting particle's entering into the light detection region" or "such that the number of light-emitting particles covered in each time section will be substantially not more than one particle" means that the predetermined width is set such that the number of light-emitting particles found in most of the time sections will be not more than one particle, namely, the existence of a time section covering two or more light-emitting particles is allowed in the range of error. According to this structure, when one time section where the light from a light-emitting particle exists is determined, in most cases, it can be judged that a light signal included in a time section is a light signal from one light-emitting particle, whereby the existence of one light-emitting particle can be confirmed, and therefore, the process for detecting a light-emitting particle individually becomes easy advantageously.

When a light-emitting particle moving at random in a sample solution becomes individually detectable as described above, various information on conditions of the light-emitting particle within the solution will be acquired. Concretely, for example, in the inventive device, the signal processor may be designed to count the number of the light-emitting particles detected during the moving of the position of the light detection region by counting the number of the individually detected light signals of the light-emitting particles (The Counting of light-emitting particles). In that case, as mentioned above, when that a light-emitting particle is individually detected using the characteristic value of light intensity in each time section of a predetermined width, the number of time sections of a predetermined width having a light signal from a light-emitting particle corresponds to the number of light-emitting particles, and therefore the number of the light-emitting particles detected during the moving of the position of the light detection region is counted by counting the number of time sections of a predetermined width having a light signal from a light-emitting particle. According to this structure, by associating the number of light-emitting particles with the moving amount of the position of the light detection region, the information on the number density or concentration of the light-emitting particle in the sample solution will be acquired. Especially, by determining the whole volume of the moving track of the position of the light detection region by an arbitrary method, for example, by moving the position of the light detection region at a predetermined speed, the number density or concentration of the light-emitting particle can be concretely computed. Of course, instead of determining directly the absolute number density value or concentration value, the relative ratio of the number density or concentration to a plurality of sample solutions or a standard sample solution to be a reference of a concentration or a number density may be computed.

Moreover, in the above-mentioned inventive device, the moving speed of the position of the light detection region in the sample solution is appropriately changed based on the characteristic of the light-emitting particle or the number density or concentration of the light-emitting particle in the sample solution. As understood by ones ordinarily skilled in the art, the condition of detected light from a light-emitting particle may change in accordance with the characteristic of the light-emitting particle or the number density or concentration of the light-emitting particle in a sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured with precisely or sufficient sensitivity.

Furthermore, in the inventive device, the moving speed of the position of the light detection region in the sample solution is preferably set to be higher than the diffusional moving velocity of a light-emitting particle to be a detected object (the average moving speed of a particle owing to the Brownian motion). As explained above, the inventive device detects light emitted from a light-emitting particle when the light detection region passes through the position where the light-emitting particle exists, thereby detecting the light-emitting particle individually. However, when the light-emitting particle moves at random owing to the Brownian motion to move into and out of the light detection region multiple times, the light signal from one light-emitting particle (showing the existence of the light-emitting particle) will be detected multiple times, and therefore it would becomes difficult to make the existence of one light-emitting particle associated with the detected light signal. Then, as described above, the moving speed of the light detection region is set higher than the diffusional moving velocity of the light-emitting particle, and thereby it becomes possible to make one light-emitting particle correspond to one light signal (indicating the existence of a light-emitting particle). In this regard, since the diffusional moving velocity differs depending upon a light-emitting particle, preferably, the inventive device may be designed to be capable of changing the moving speed of the light detection region appropriately according to the characteristics (especially, the diffusion constant) of the light-emitting particle as described above.

The moving of the position of the light detection region may be done in an arbitrary way. For example, the position of the light detection region may be changed by changing the optical path using a galvanomirror employed in the laser scan type light microscope, or while the light detection region is immobilized, the position of the light detection region in the sample solution may be moved by moving the position of the sample solution (moving the stage of a microscope). The movement track of the position of the light detection region may be set arbitrarily, for example, which may be selected from circular, elliptical, rectangular, straight and curvilinear ones.

The processes of the optical analysis technique of performing light detection together with moving the position of the light detection region in a sample solution, and detecting individually the light signal from each light-emitting particle in the above-mentioned inventive device is realizable also by a general purpose computer. Therefore, according to another aspect of this invention, there is provided a computer readable storage device having a computer program product including programmed instructions for optical analysis for detecting light from a light-emitting particle dispersed and moving at random in a sample solution by using an optical system of a confocal microscope or a multiphoton microscope, said programmed instructions causing a computer to perform steps of: moving a position of a light detection region of the optical system in the sample solution; detecting light from the light detection region during moving the position of the light detection region in the sample solution to generate time series light intensity data; computing a characteristic value of light intensity indicating a presence or an absence of light from a single light-emitting particle in every time section of a predetermined width in the time series light intensity data; and detecting individually a light signal from each light-emitting particle, using the characteristic value of light intensity in each of the time sections of the predetermined width.

Also, this computer program may comprise the step of counting the number of the light-emitting particles detected during the moving of the position of the light detection region by counting the number of the individually detected light signals from the light-emitting particle or by counting the number of the time sections of the predetermined width having a light signal from a light-emitting particle and/or the step of determining the number density or concentration of the light-emitting particle in the sample solution based on the number of the detected light-emitting particles. Typically, in the step of detecting the light from the light detection region to generates time series light intensity data, the light from the light detection region is detected by photon counting, and in that case, the time series light intensity data is time series photon count data. In the step of moving the position of the light detection region, the position of the light detection region may be moved at a predetermined velocity or a velocity faster than a diffusional moving velocity of the light-emitting particle, and the moving speed of the position of the light detection region may be set based on a characteristic of the light-emitting particle or the number density or concentration of the light-emitting particle in the sample solution. The movement track of the position of the light detection region may be selected from circular, elliptical, rectangular, straight and curvilinear ones.

Furthermore, also in the above-mentioned computer program, the characteristic value of light intensity in the time section of the predetermined width may be a value which, when light from a single light-emitting particle exists, becomes larger than when no light from a single light-emitting particle exist, and it may be judged that the light signal from the light-emitting particle exists in the time section of the predetermined width when the characteristic value of light intensity is larger than a predetermined threshold value. Concretely, such a characteristic value may be employed from either of the integrated value of the light intensity, the center value of the light intensity, the average value of the light intensity, the standard deviation of the light intensity, the variance of the light intensity, the entropy of the light intensity, the maximum value of the light intensity and the number of particles computed from the value of an autocorrelation function of the light intensity with a correlation time being set to 0, in the time section of the predetermined width. Especially, when the time series light intensity data is time series photon count data, the characteristic value of light intensity may be a value selected from a group of a total value of photon counts, a center value of photon counts, an average value of photon counts, a standard deviation of photon counts, a variance of photon counts, an entropy of photon counts, a maximum value of photon counts and a the number of particles computed from an autocorrelation function value of photon counts with a correlation time being set to 0, in the time section of the predetermined width. Moreover, preferably, the predetermined width of the time section as described above is set to be substantially longer than a time width required for an interval from a time of one light-emitting particle's entering into the light detection region to a time of its exiting therefrom, and also substantially shorter than a time width from a time of one light-emitting particle's entering into the light detection region to a time of a different light-emitting particle's entering into the light detection region.

Furthermore, according to the above-mentioned inventive device or computer program, there is realized a novel optical analysis method of detecting individually a light signal from each light-emitting particle through detecting light together with moving the position of the light detection region in a sample solution. Thus, the inventive optical analysis method of detecting light from a light-emitting particle dispersed and moving at random in a sample solution by using an optical system of a confocal microscope or a multiphoton microscope is characterized by comprising steps of: moving a position of a light detection region of the optical system in the sample solution; detecting light from the light detection region during moving the position of the light detection region in the sample solution to generate time series light intensity data; computing a characteristic value of light intensity indicating a presence or an absence of light from a single light-emitting particle in every time section of a predetermined width in the time series light intensity data; and detecting individually a light signal from each light-emitting particle, using the characteristic value of light intensity in each of time sections of the predetermined width.

This method may also comprise the step of counting the number of the light-emitting particles detected during moving the position of the light detection region by counting the number of the individually detected light signals from the light-emitting particle or by counting the number of the time sections of the predetermined width having a light signal from a light-emitting particle and/or the step of determining the number density or concentration of the light-emitting particle in the sample solution based on the number of the detected light-emitting particles. Typically, in the step of detecting the light from the light detection region to generates time series light intensity data, the light from the light detection region is detected by photon counting, and in that case, the time series light intensity data is time series photon count data. Further, in the step of moving the position of the light detection region, the position of the light detection region may be moved at a predetermined velocity or a velocity faster than a diffusional moving velocity of the light-emitting particle, and the moving speed of the position of the light detection region may be set based on a characteristic of the light-emitting particle or the number density or concentration of the light-emitting particle in the sample solution. The movement track of the position of the light detection region may be selected from circular, elliptical, rectangular, straight and curvilinear ones.

Furthermore, also in the above-mentioned method, the characteristic value of light intensity in the time section of the predetermined width may be a value which, when light from a single light-emitting particle exists, becomes larger than when no light from a single light-emitting particle exist, and it may be judged that the light signal from the light-emitting particle exists in the time section of the predetermined width when the characteristic value of light intensity is larger than a predetermined threshold value. Concretely, such a characteristic value may be employed from either of the integrated value of the light intensity, the center value of the light intensity, the average value of the light intensity, the standard deviation of the light intensity, the variance of the light intensity, the entropy of the light intensity, the maximum value of the light intensity and the number of particles computed from the value of an autocorrelation function of the light intensity with a correlation time being set to 0, in the time section of the predetermined width. Especially, when the time series light intensity data is time series photon count data, the characteristic value of light intensity may be a value selected from selected from a group of a total value of photon counts a center value of photon counts, an average value of photon counts, a standard deviation of photon counts, a variance of photon counts, an entropy of photon counts, a maximum value of photon counts and the number of particles computed from an autocorrelation function value of photon counts with a correlation time being set to 0, in the time section of the predetermined width. Moreover, preferably, the predetermined width of the time section as described above is set to be substantially longer than a time width required for an interval from a time of one light-emitting particle's entering into the light detection region to a time of its exiting therefrom, and also substantially shorter than a time width from a time of one light-emitting particle's entering into the light detection region to a time of a different light-emitting particle's entering into the light detection region.

Effects of Invention

The optical analysis technique realized by the above-mentioned inventive device, method or computer program employs, for its light detecting mechanism itself, a structure to detect light from a light detection region in a confocal microscope or a multiphoton microscope similarly to the cases of optical analysis techniques, such as FCS, FIDA and PCH, and thus the amount of a sample solution may be similarly small. However, since no statistical procedure of computing the fluorescence intensity fluctuation is performed in the present invention, the inventive optical analysis technique is applicable to a sample solution in which the number density or concentration of a light-emitting particle is substantially lower than the level required for the optical analysis techniques, such as FCS, FIDA and PCH.

Moreover, since each light-emitting particle dispersed or dissolved in a solution is individually detected in this invention, it becomes quantitatively possible by using the information thereon to conduct the counting of light-emitting particles, the computation of the concentration or number density of the light-emitting particle in a sample solution or the acquisition of the information on the concentration or number density. For example, although patent documents 5 and 6 could acquire the correlation between the aggregate in the frequency of fluorescence signals having an intensity beyond a predetermined threshold value within a predetermined time and the number of particles of fluorescent molecules, etc. in a sample solution, it is impossible to grasp the dynamic behavior of a particle passing through the measuring region (whether a particle passes straight through the measuring region or dwells within the measuring region), and therefore the correspondence between a fluorescence signal having an intensity higher than a predetermined threshold value and a particle passing through the measuring region is not clear, so that the counting of light-emitting particles was theoretically impossible and it was difficult to determine precisely the concentration of particles in a sample solution. However, since, according to this invention, a light-emitting particle passing through a light detection region is made associated with a time of arrival of a light signal of the light-emitting particle to the light detector in 1 to 1 manner so that one light-emitting particle will be detected at one time, the counting of light-emitting particles dispersed and moving at random in a solution becomes possible, and it becomes possible to determine the concentration or number density of the particle in a sample solution precisely as compared with the conventional art.

The inventive optical analysis technique is typically used for analyses of conditions in a solution of biological particulate objects, such as biological molecules, e.g., a protein, a peptide, a nucleic acid, a lipid, a sugar chain, an amino acid or an aggregate of these, a virus and a cell, although it may be used for analyses of conditions of non-biological particles in a solution (for example, an atom, a molecule, a micelle, a metallic colloid, etc.), and it should be understood that such cases are included in the scope of the present invention, also.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device according to the present invention. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism for moving the horizontal position of a micro plate to move the position of a light detection region in a sample solution.

FIGS. 2A and 2B are a schematic diagram explaining the principle of the light detection by the optical analysis technique according to the present invention and a schematic diagram of the variation of the measured light intensity with time, respectively. FIG. 2C is a drawing explaining about the principle of detecting, from the light intensity data, individually the light from a light-emitting particle. FIG. 2D shows the relation between the predetermined width of a time section and the probability that the light of two or more light-emitting particles is entering simultaneously (the ratio of a plurality of light-emitting particles included in one time section of a predetermined width ω).

FIGS. 3A and 3B are a drawing of a model in the case that a light-emitting particle cross a light detection region owing to Brownian motion and a diagram showing the example of the variation of the photon counts (light intensity) with time in this case, respectively.

FIGS. 4A and 4B are a drawing of a model in the case that a light-emitting particle crosses a light detection region by moving the position of the light detection region in a sample solution at a velocity faster than the diffusional moving velocity of the light-emitting particle, and a diagram showing the example of the variation of the photon counts (light intensity) with time in this case, respectively.

Figure 8A:
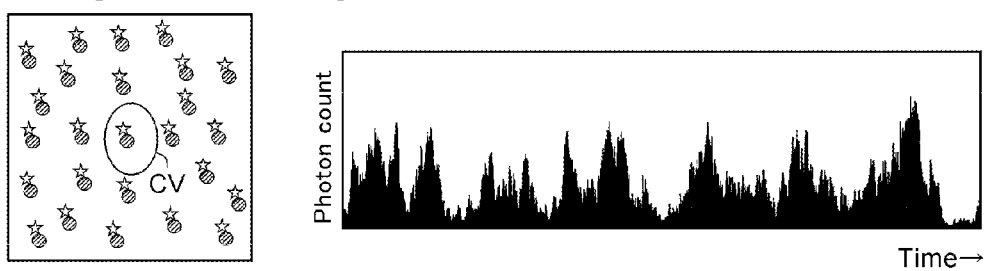
Figure 8B:
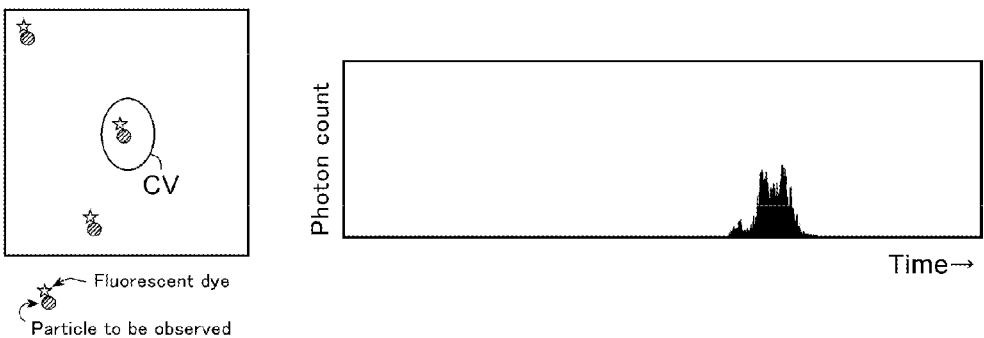

FIG. 8 shows examples of the time variation of the photon count (light intensity) obtained in a conventional optical analysis technique computing fluorescence intensity fluctuation, where 8A shows a case that the particle concentration is at a level providing a sufficient precision in the measurement, and 8B shows a case that the particle concentration in a sample is significantly lower than the case of (A).

| Explanations of Reference Numerals | |
|---|---|
| 1 | Optical analysis device (confocal microscope) |
| 2 | Light source |
| 3 | Single mode optical fiber |
| 4 | Collimating lens |
| 5 | Dichroic mirror |
| 6, 7, 11 | Reflective mirror |
| 8 | Objective |
| 9 | Micro plate |
| 10 | Well (sample solution container) |
| 12 | Condenser lens |
| 13 | Pinhole |
| 14 | Barrier filter |
| 15 | Multi-mode optical fiber |
| 16 | Photodetector |
| 17 | Mirror deflector |
| 17a | Stage position changing apparatus |
| 18 | Computer |

DESCRIPTION OF EMBODIMENTS

In the followings, preferable embodiments of the present invention are described in detail.

The Structure of an Optical Analysis Device

The basic structure of the optical analysis device which realizes the inventive optical analysis technique may be a device formed by combining an optical system of a confocal microscope and a photodetector as schematically illustrated in FIG. 1A, with which FCS, FIDA, etc. can be performed. Referring to the drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are fluorescent particles or particles to which a light emitting label such as a fluorescent dye is attached, are dispersed or dissolved, and when a light-emitting particle enters into the excitation region, the light-emitting particle during dwelling in the excitation region is excited, emitting light. The emitted light (Em), after passing through the objective 8 and the dichroic mirror 5, is reflected on the mirror 11 and condensed by a condenser lens 12, and then the light passes through the pinhole 13; transmits through a barrier filter 14 (where light components only in a specific wavelength band region are selected); and is introduced into a multimode fiber 15, reaching to a photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region in this light analysis device, whose effective volume is usually about 1-10 fL (Typically, the light intensity is spread in accordance with a Gaussian distribution having the peak at the center of the region. The effective volume is a volume of an approximate ellipsoid bordering a surface where the light intensity reduced to $1/e^2$ of the peak intensity.), which is called as "confocal volume". Moreover, since the light from one light-emitting particle, for example, the faint light from one fluorescent dye molecule, is detected in this invention, preferably, a super high sensitive photodetector, usable for the photon counting, is used for the photodetector 16. When the detection of light is performed by the photon counting, the measurement of light intensity is sequentially performed in the manner of measuring the number of photons arriving at the photodetector for every predetermined unit time (BIN TIME) in a predetermined term. Thus, in this case, the time series light intensity data is time series photon count data.

Furthermore, in the optical system of the above-mentioned optical analysis device, there is provided a mechanism for scanning the inside of the sample solution with the light detection region, i.e., the focal region, namely for moving the position of the light detection region within the sample solution. For this mechanism for moving the position of the light detection region, for example, as schematically illustrated in FIG. 1C, there may be employed a mirror deflector 17 which changes the direction of the reflective mirror 7 (Type of moving the absolute position of the light detection region). This mirror deflector 17 may be the same as that of a galvanomirror device equipped on a usual laser scan type microscope. Or, alternatively, as illustrated in FIG. 1D, there may be employed a stage position changing apparatus 17a to move the horizontal position of the container 10 (micro plate 9) into which a sample solution has been dispensed for moving the relative position of the light detection region in the sample solution (Type of moving the absolute position of a sample solution). Even in either of the types, in order to attain a desired moving pattern of the position of the light detection region, the mirror deflector 17 or the stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (In the program in the computer 18, it may be designed so that various moving patterns can be selected.). In this regard, although not illustrated, the position of the light detection region may be moved in the vertical direction by moving the objective 8 up and down.

In the case that the light-emitting particle used as an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that the light-emitting particle used as an object to be observed emits light owing to a chemiluminescence or bioluminescence phenomenon without excitation light, the optical system 2-5 for generating excitation light may be omitted. When the light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wave length of the excitation light can be selected appropriately in accordance with the excitation wave length of the light-emitting particle. Similarly, two or more photodetectors 16 may also be provided so that, when the sample contains two or more kinds of light-emitting particles whose wave lengths differ from one another, the respective lights from them can be detected separately in accordance with the wave lengths.

The Principle of the Inventive Optical Analysis Technique

Spectral analysis techniques, such as FCS and FIDA, are advantageous in that the required sample amount is extremely small and a test can be performed promptly as compared with the conventional biochemical analytical techniques. However, in these spectral analysis techniques such as FCS and FIDA, the concentration and characteristics of a particle to be observed are principally computed based on the fluorescence intensity fluctuation, and therefore, in order to obtain accurate measurement results, the concentration or number density of the particle to be observed in a sample solution should be at a level where about one particle to be observed always exists in a light detection region CV during the fluorescence intensity measurement as schematically drawn in FIG. 8A so that significant light intensity (photon count) can be always detected in the measuring term as shown in the right-hand side of the drawing. When the concentration or number density of the particle to be observed is lower than that, for example, at the level where the particle to be observed rarely enters into the light detection region CV as drawn on FIG. 8B, no significant light intensity (photon count) would appear in a part of the measuring term as illustrated on the right-hand side of the drawing, and thus, accurate computation of light intensity fluctuation would become difficult. Also, when the concentration of the particle to be observed is significantly lower than the level where about one particle to be observed always exists in the inside of the light detection region during the measurement, the calculation of light intensity fluctuation would become subject to the influence of the background, and the measuring term should be made long in order to obtain the significant quantity of the light intensity data (photon count), sufficient for the calculation.

Then, in the present invention, there is proposed an optical analysis technique based on a new principle which enables the detection of characteristics, such as the number density or concentration of a particle to be observed, even when the concentration of the particle to be observed is lower than the level requested in the above-mentioned spectral analysis techniques, such as FCS and FIDA.

In the inventive optical analysis technique, briefly speaking, as the processes to be performed, the light detection is performed together with moving the position of the light detection region CV in a sample solution, namely, scanning the inside of the sample solution with the light detection region CV by driving the mechanism (mirror deflector 17 or stage position changing apparatus 17*a*) for moving the position of the light detection region as schematically drawn in FIG. 2. Then, for example, as in FIG. 2A, during the moving of the light detection region CV (in the drawing, time to-t2), when the light detection region CV passes through a region where one light-emitting particle (In the drawing, a fluorescent dye) exists (t1), a significant light intensity (Em) will be detected as a pulse form signal, as drawn in FIG. 2B. Thus, by detecting, one by one, each significant light intensity, i.e. each pulse form signal, appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. It should be understood that, in the principle of this inventive optical analysis technique, no statistical calculation processes, such as the calculation of the fluorescence intensity fluctuation, are conducted and the light-emitting particles are one by one detected, and therefore, the information about the concentration or number density of the light-emitting particle is acquirable even in a sample solution with a low concentration of the light-emitting particle (particle to be observed) at the level where no sufficiently precise analysis is available in FCS and FIDA.

Figure 2A:
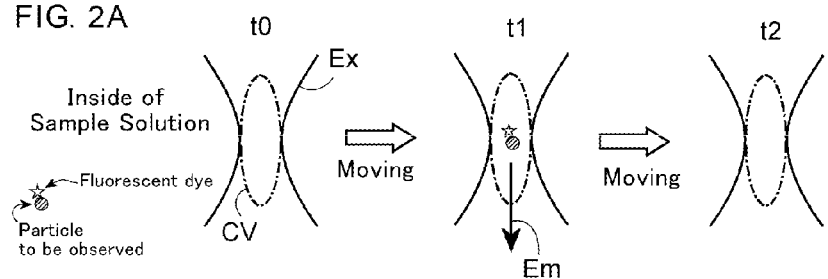
Figure 2B:
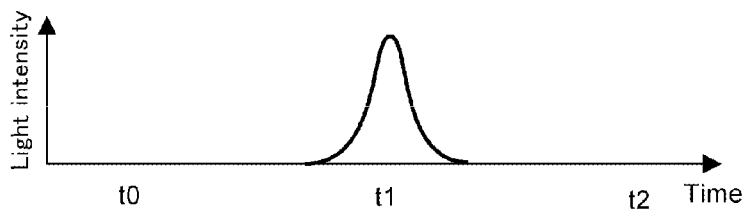
Figure 2C:
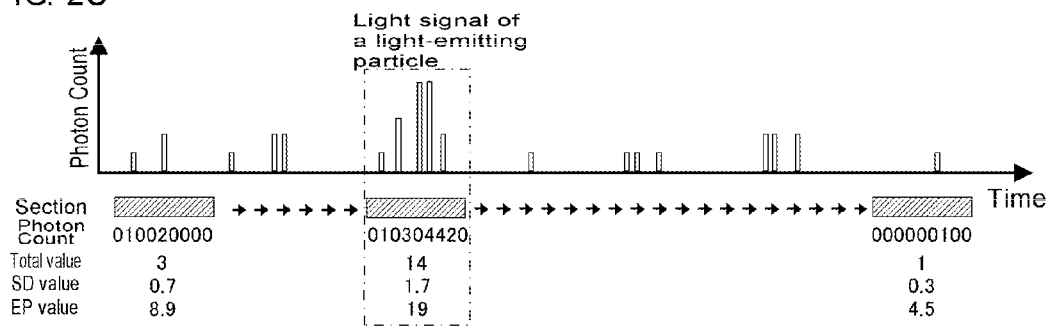

In this regard, in an actual light intensity data (photon count data), as illustrated in FIG. 2C, there exists noise (the heat noise of a photodetector, background light) other than the light from light-emitting particles, and thus, it is required to detect an existence of a light signal from a light-emitting particle while distinguishing the light signal from the light-emitting particle from noise. Thus, as one of such ways of extracting an existence of a light signal from a light-emitting particle, in this embodiment, a characteristic value of light intensity indicating the presence or absence of light from a single light-emitting particle is sequentially computed in every time section of a predetermined width in the time series light intensity data by means of the light intensity values (photon counts) in each time section. By referring to the magnitude of that characteristic value of light intensity, whether or not a light signal from a single light-emitting particle exists can be detected for every time section of a predetermined width, and thereby a light-emitting particle can be detected one by one. Typically, the characteristic value of the light intensity indicating the presence or absence of a light from a single light-emitting particle may be an arbitrary value which increases in the presence of a signal of light from a single light-emitting particle as compared with a case that no signal of light from a single light-emitting particle exist (when only noise exists), and for instance, the characteristic value may be the integrated value of the light intensity, the center value of the light intensity, the average value of the light intensity, the standard deviation of the light intensity (SD value), the variance of the light intensity, the entropy of the light intensity (EP value), the maximum value of the light intensity and the number of particles computed from the value of an autocorrelation function of the light intensity with the correlation time being set to 0, etc., in a time section of a predetermined width. Especially, in this embodiment, since the light intensity data is the photon count data according to the photon counting, the characteristic value may be a value selected from a group of a total value of photon counts, a center value of photon counts, an average value of photon counts, a standard deviation of photon counts, a variance of photon counts, an entropy of photon counts, a maximum value of photon counts and a the number of particles computed from an autocorrelation function value of photon counts with a correlation time being set to 0, in a time section of a predetermined width.

Further, preferably, the predetermined width of the time section for the computation of the above-mentioned characteristic value is set to be substantially longer than a time width required for an interval from a time of one light-emitting particle's entering into the light detection region to a time of its exiting therefrom, and also substantially shorter than a time width from a time of one light-emitting particle's entering into the light detection region to a time of a different light-emitting particle's entering into the light detection region. By setting the predetermined width so, one time section in which a light signal of a light-emitting particle exists corresponds to an existence of one light-emitting particle, namely, the one to one relation between a time section and the existence of a light-emitting particle is established, and thereby the process in counting light-emitting particles becomes advantageously easy. (If the predetermined width of the time section is shorter than a time width required for an interval from a time of one light-emitting particle's entering into the light detection region to a time of its exiting therefrom, the light signal of one light-emitting particle would exist over two or more time sections, and thus, a process for making a plurality of time sections correspond to one light-emitting particle would be required. On the other hand, if the predetermined width of the time section is longer than a time width from a time of one light-emitting particle's entering into the light detection region to a time of a different light-emitting particle's entering into the light detection region, the light signals of a plurality of light-emitting particles would exist in one time section, and thereby it becomes difficult to detect one light-emitting particle one by one.

When it is assumed that a light-emitting particle passes the center of a light detection region linearly (see "(1) Measurement of the light intensity of a sample solution", described below, and FIG. 4, for example, using the diameter 2Wo and the moving speed, u, of the light detection region, the lower limit ωlow of the above-mentioned predetermined width may be set as:

$$\omega low = 2Wo/u \quad (1).$$

The upper limit ωhigh of the predetermined width is to be a predetermined width in which the number of light-emitting particles included in each time section becomes substantially not more than one. The upper limit ωhigh of the predetermined width can be determined in one of the following ways. (1) The case that it is assumed that light-emitting particles are dispersed uniformly in a sample solution The number of light-emitting particles, n, detected during the moving of the light detection region in a time section of a predetermined width ω is given by $$n = cN_A Su\omega \quad (2a),$$

where c is the mole concentration of the light-emitting particle, $N_A$ is the Avogadro's number and S is a cross sectional area of the light detection region. Approximating that $S \sim \pi Wo^2$, and assuming that one light-emitting particle exists (n=1) in a time section of the predetermined width ω, the predetermined width ω is given by:

$$\omega = 1/(cN_A \pi Wo^2 u) \quad (2b).$$

Therefore, using an expected concentration c of the light-emitting particle, the predetermined width ωhigh may be set as the value ω computed with the expression (2b), or a value smaller than it in consideration of the dispersion of the existence positions of the light-emitting particles.

(2) The case that it is assumed that a light-emitting particle enters into a time section of a predetermined width in accordance with the Poisson distribution The average number of light-emitting particles, n, detected during the moving of the light detection region in a time section of a predetermined width ω is given by the above-mentioned expression (2a). On the other hand, the probability pk that the number of light-emitting particles appearing in a time section of a predetermined width ω is k becomes:

[Expression 1]

$$pk = \frac{e^{-n} n^k}{k!} \quad (2c)$$

and thus, the probability $p_{>1}$, that the number of the light-emitting particles appearing in a time section of a predetermined width ω is two or more, i.e., the ratio that two or more light-emitting particles are included in one time section of the predetermined width ω, becomes:

[Expression 2]

$$p_{>1} = 1 - \sum_{k=0}^{1} \frac{e^{-n} n^k}{k!} \quad (2d)$$

Figure 2D:
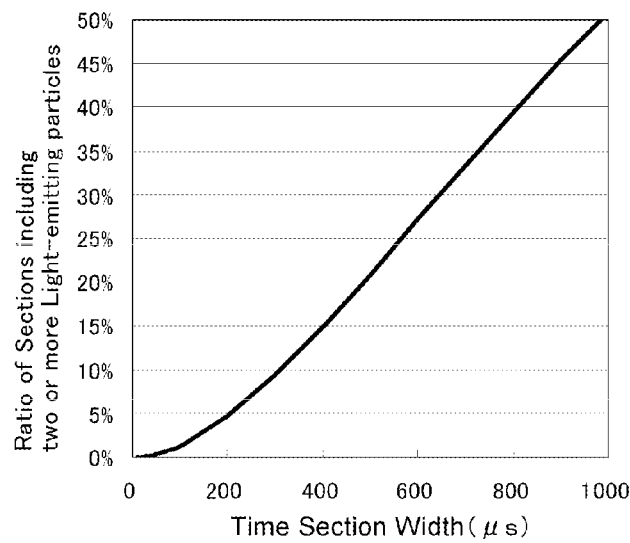

FIG. 2D is a diagram showing an example of change of the expression (2d) against the predetermined width ω (computed with c=10 pM, u=15 mm/s, Wo=1 μm). With reference to the diagram, in the illustrated example, it is understood that 5% of time sections covers a plurality of light-emitting particles when the predetermined width is set to ω=200 μsec. Thus, the predetermined width ωhigh may be set to a predetermined width ω providing an allowable error in the expression (2d), using an expected light-emitting particle concentration, c.

Operations of the Inventive Light Analysis Device and Operation Processes

Concretely, in the optical analysis with the inventive optical analysis device 1 as illustrated in FIG. 1A, there are conducted (1) a process of measuring the light intensity of a sample solution containing light-emitting particles (particles to be observed) and (2) a process of analyzing the measured light intensity.

(1) Measurement of the Light Intensity of a Sample Solution

The particle used as the object to be observed in the inventive optical analysis technique may be an arbitrary particle as long as it is dispersed and moving at random in a sample solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecule. When the particle used as the object to be observed is not a light-emitting particle, a particle prepared by attaching a light emitting label (a fluorescence molecule, a phosphorescence molecule, a chemiluminescence or bioluminescent molecule) with the particle to be observed in an arbitrary way is used. The sample solution is typically an aqueous solution, although not limited thereto and an organic solvent and other arbitrary liquid may be used.

The measurement of the light intensity in the inventive optical analysis may be performed in the same manner as the measurement process of the light intensity in FCS or FIDA except driving the mirror deflector 17 or stage position changing apparatus 17a to move the position of the light detection region within the sample solution (to scan in the sample solution) during the measurement. In the operation process, typically, after dispensing a sample solution into the well(s) 10 of the micro plate 9 and putting it on the stage of the microscope, when a user inputs to the computer 18 a command of a measurement start, the computer 18 executes programs memorized in a storage device (not shown)(the process of moving the position of the light detection region in the sample solution, and the process of detecting light from the light detection region during the moving of the position of the light detection region and generating time series light intensity data), and then illuminating the light detection region in the sample solution with the excitation light and measuring light intensity will be started. During this measurement, under the control of the operation process of the computer 18 according to the programs, the mirror deflector or stage position changing apparatus 17a drives the mirror 7 (galvanomirror) or the micro plate 9 on the stage of the microscope to move the position of the light detection region in the well 10, and simultaneously with this, the photodetector 16 sequentially converts the detected light into an electric signal and transmits it to the computer 18, which generates the time series light intensity data from the transmitted light signals and store it in an arbitrary manner. In this regard, the photodetector 16 is typically a super high sensitive photodetector which can detect an arrival of a single photon, and thus, when the light detection is done by the photon counting, the time series light intensity data may be time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light-emitting particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

Figure 3A:
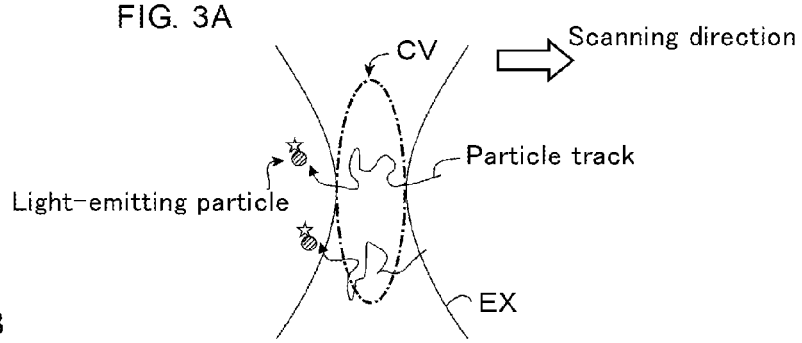
Figure 3B:
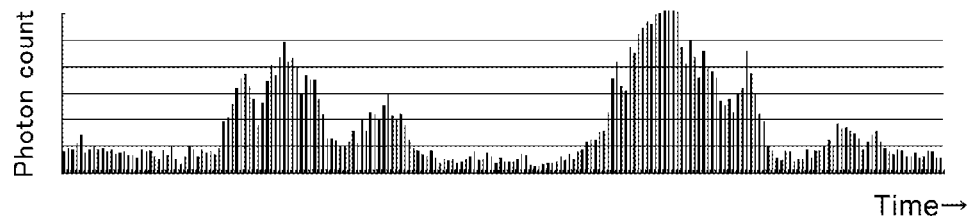

By the way, regarding the moving speed of the position of the light detection region, in order to perform quantitatively precisely individual detection of the light-emitting particles from the measured time series light intensity data or the counting of the number of the light-emitting particles, it is preferable that the moving speed is set to a value faster than the moving speed in the random motion, i.e., Brownian motion of a light-emitting particle. Since the particle to be observed in the inventive optical analysis technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 3A, whereby the light intensity changes at random as shown in FIG. 3B (As already noted, the excitation light intensity in the light detection region is reduced from the peak at the center of the region toward its outside.), so that it becomes difficult to determine a significant light intensity change corresponding to each light-emitting particle. Then, preferably, as drawn in FIG. 4A, the moving speed of the position of the light detection region is set to be faster than the average moving speed of a particle by the Brownian motion (diffusional moving velocity) so that a particle will cross the light detection region in an approximately straight line and thereby the profile of the change of the light intensity corresponding to each light-emitting particle becomes almost uniform in the time series light intensity data as illustrated in FIG. 4B (When a light-emitting particle passes through the light detection region in an approximately straight line, the profile of the light intensity change is similar to the excitation light intensity distribution.) and the correspondence between each light-emitting particle and light intensity can be easily determined.

Concretely, the time $\Delta t$ required for a light-emitting particle having a diffusion coefficient D to pass through the light detection region of radius Wo (confocal volume) by Brownian motion is given from the expression of the relation of mean-square displacement:

$$(2Wo)^2 = 6D \cdot \Delta t \quad (4)$$

as:

$$\Delta t = (2Wo)^2/6D \quad (5),$$

and thus, the velocity of the light-emitting particle moving by Brownian motion (diffusional moving velocity) Vdif, becomes approximately $$V\text{dif} = 2Wo/\Delta t = 3D/Wo \quad (6)$$

Then, with reference to this, the moving speed of the position of the light detection region may be set to a value sufficiently faster than Vdif. For example, when the diffusion coefficient of a particle to be observed is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, e.g. 15 mm/s. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(2) Analysis of Light Intensity

When the time series light intensity data of a sample solution are obtained by the above-mentioned processes, an analysis of the light intensity as described below may be performed in the computer 18 through processes in accordance with programs memorized in a storage device (the process of computing a characteristic value of light intensity indicating the presence or absence of the light from a single light-emitting particle for every time section of a predetermined width in the time series light intensity data, and the process of detecting individually the light signal of each light-emitting particle based on the characteristic value of the light intensity for every time section of a predetermined width).

(i) Detection of One Light-Emitting Particle

Figure 4A:
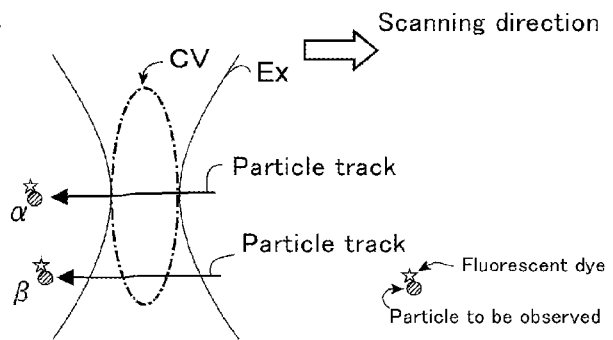
Figure 4B:
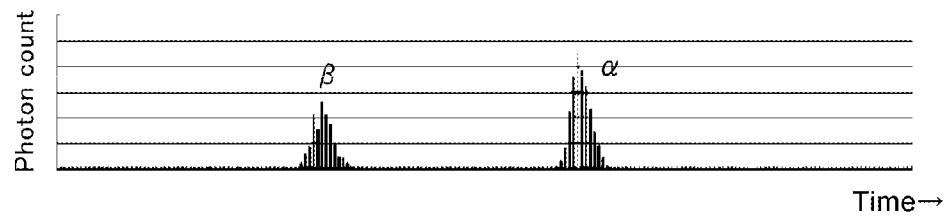

When the track of one light-emitting particle in its passing through the light detection region is approximately straight as shown in FIG. 4A, the light intensity variation corresponding to the light-emitting particle in the time series light intensity data has a profile reflecting the light intensity distribution in the light detection region (determined by the optical system) (usually approximately bell shape) as schematically drawn in FIG. 4B, which variation is significantly different from that of a period in the data in which period no light-emitting particle has passed (a condition that noise generates at random). Thus, as already noted, in this embodiment, there is computed a characteristic value of light intensity for every time section of a predetermined width in time series light intensity data. When the time series light intensity data is the time series photon count data, as described above, the characteristic value of light intensity may be a value selected from a group of a total value of photon counts, a center value of photon counts, an average value of photon counts, a standard deviation of photon counts, a variance of photon counts, an entropy of photon counts, a maximum value of photon counts and the number of particles computed from an autocorrelation function value of photon counts with a correlation time being set to 0, in a time section of a predetermined width.

Regarding the respective characteristic values, more in details, the total value of photon counts is the total value of the photon counts in a time section of a predetermined width. Since the total value in a time section where a light signal of a light-emitting particle exists increases by the number of photons from the light-emitting particle from the total value in the other time sections, it can be judged that a light signal of a light-emitting particle exists in a certain time section when the magnitude of the total value of the certain time section is larger than a predetermined threshold value.

The center value and the maximum value of photon counts each are the center value and the maximum value of the photon counts found in a time section of a predetermined width. Since a photon count during a period when the light of a light-emitting particle has arrived at a photodetector becomes larger than in a case that only usual noises occur, the center value and the maximum value also increase in a time section where a light signal of a light-emitting particle exists. Thus, it can be judged that a light signal of a light-emitting particle exists in a certain time section when the magnitude of the center value or the maximum value in the certain time sections is larger than a predetermined threshold value.

The average value of photon counts is the time average value of the photon counts in a time section of a predetermined width. As noted above, since the total value in a time section where a light signal of a light-emitting particle exists increases by the number of the photons from the light-emitting particle from the total value in the other time sections, the time average value of photon counts in the time section of the predetermined width also increases. Thus, it can be judged that a light signal of a light-emitting particle exists in a certain time section when the magnitude of the average value of the certain time section is larger than a predetermined threshold value.

The standard deviation value, variance value and entropy value of photon counts each are the standard deviation value and variance value in the time average, and the entropy of information content of photon counts in a time section of a predetermined width, and these each are a characteristic value indicating the degree of the dispersion of the temporal variation of the photon count found within a time section of a predetermined width. When a light signal of a light-emitting particle exists in a certain time section, the time variation of photon count becomes more intense as compared with the other time sections. Thus, since the standard deviation value, variance value and entropy value of photon counts in a time section where a light signal of a light-emitting particle exists increase as compared with the respective values in the other time sections, it can be judged that a light signal of a light-emitting particle exists in a certain time section when each of the values in the certain time section is larger than a predetermined threshold value. In this regard, regarding the entropy value of photon counts, when the probability that the photon count is x at a certain time (BIN TIME) is px, using the number of the time points ix at which the photon count is x, in a certain time section, the entropy value of photon counts is the value given by:

$$-\log_2(p0^{i0} \cdot p1^{i1} \cdot \ldots \cdot px^{ix} \cdot \ldots \cdot pn^{in}) \quad (7)$$

Usually, the probability px that the photon count is x satisfies $p0 > p1 > p2 > \ldots > px \ldots > pn$. Although the entropy value in a section where only noise exists is approximately $-\log_2(p0^{i0} \cdot p1^{i1} p2^{i2})$, it becomes $-\log_2(p0^{i0} \cdot p1^{i1} \cdot p2^{i2} \cdot p3^{i3} \cdot p4^{i4})$, etc., in a section where a light signal of a light-emitting particle exists, and thus, the value increases.

The number of particles in a time section of a predetermined width, computed from an autocorrelation function value of photon counts with a correlation time being set to 0, is the quantity equivalent to the number of particles in the time section. According to the theory of FCS, the autocorrelation function $C(\tau)$ of light intensity is given by:

[Expression 3]

$$C(\tau) = 1 + \frac{1}{N}\left(1 + \frac{\tau}{\tau_D}\right)^{-1}\left(1 + \frac{\tau}{AR^2 \tau_D}\right)^{-1/2} \quad (8)$$

(where $\tau_D$ is a translational diffusion time, AR is a structure parameter and N is the number of particles.). In the above-mentioned expression, the number of particles N is given by $1/(C(0)-1)$, using $C(0)$ at the time of the correlation time $\tau=0$. Since it is thought that this number of particles is the number of particles found in each time section, it can be judged that a light signal of a light-emitting particle exists in a time section when the number of particles is larger than a predetermined threshold value, similarly to the above-mentioned characteristic values.

(ii) Counting of Light-Emitting Particles

In the above-mentioned process of the detection of a light-emitting particle, when the predetermined width of the time section is set to be substantially longer than a time width required for an interval from a time of one light-emitting particle's entering into the light detection region to a time of its exiting therefrom, and also substantially shorter than a time width from a time of one light-emitting particle's entering into the light detection region to a time of a different light-emitting particle's entering into the light detection region, one light-emitting particle corresponds to one time section judged as a time section in which a light signal of a light-emitting particle exists, and therefore, the number of light-emitting particles is determined by counting the number of these time sections.

(iii) Determination of the Number Density or Concentration of a Light-Emitting Particle When the counting of light-emitting particles has been done, the number density or concentration of the light-emitting particle can be determined using the volume of the whole region which the light detection region has passed through. However, the effective volume of the light detection region varies depending on the wave length of excitation light or detected light, the numerical aperture of lenses and the adjustment condition of the optical system, and therefore, it is difficult to compute the effective volume of the light detection region from the design parameter values. Then, in this embodiment, the light intensity measurement, the detection of light-emitting particles and the counting thereof are performed as explained above with a solution having a known light-emitting particle concentration (reference solution) under the same condition as that for the measurement of the sample solution to be tested, and then, from the detected number of light-emitting particles and the concentration of light-emitting particle in the reference solution, the volume of the whole region which the light detection region has passed through, i.e., the relation between the detected number and the concentration of the light-emitting particle, may be determined. Preferably, the light-emitting particle of a reference solution may be a light emitting label (fluorescent dye etc.) having the same wavelength characteristic as a particle to be observed. Concretely, for example, supposing the detected number of the light-emitting particles is N in a reference solution of the light-emitting particle concentration C, the volume Vt of the whole region which the light detection region has passed through is given by:

$$Vt = N/C \quad (9).$$

Alternatively, the plurality of solutions of different concentrations of a light-emitting particle are prepared as reference solutions and the measurement is performed for each of the solutions, and then, the average value of the computed Vt is determined as the volume Vt of the whole region which the light detection region has passed through. Thus, when Vt is given, the number density c of the light-emitting particle of the sample solution, whose counting result of the light-emitting particles is n, is given by:

$$c = n/Vt \quad (10)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (expression (9)) between concentrations C and light-emitting particle numbers N of various standard light-emitting particles for assumed moving patterns of the light detection region, so that a user of the device can appropriately use the memorized information on the relation in conducting an optical analysis.

Thus, according to the above-mentioned inventive optical analysis technique, by moving, in a sample solution, the position of a micro region, i.e. a light detection region, namely scanning the inside of the sample solution and detecting individually a light-emitting particle crossing the light detection region or conducting the counting of the light-emitting particles, where no statistical procedures, such as calculation of fluorescence intensity fluctuation, performed in FCS, FIDA, etc., are included, it becomes possible to detect a condition or a characteristic of a particle to be observed in a sample solution whose the concentration or number density of the particle to be observed is lower than the level used in FCS, FIDA, etc.

In this regard, since the inventive optical analysis technique basically uses the same optical system as FCS, FIDA, etc. it may be performed together with FCS, FIDA, etc. For example, in a case of detecting an interaction, etc. between two or more kinds of substances in a solution containing of these, when the concentration difference between substances is large, for example when the concentration of one substance is nM order and that of the other substance is pM order, there can be conducted a manner that measurement and analysis are conducted by FCS or FIDA for the substance of the higher concentration while measurement and analysis are conducted by the inventive optical analysis technique for the substance of the lower concentration. In such a case, as illustrated in FIG. 1A, it is advantageous to prepare two or more photodetectors.

In order to verify the validity of the present invention explained above, the experiments described below were conducted. In this regard, it should be understood that the following embodiments illustrate the validity of the present invention only, not intended to limit the scope of the present invention.

Embodiment 1

The concentration range of a light-emitting particle in a sample solution which can be measured by the present invention was verified using a fluorescent dye, ATTO633 (sigma Aldrich Cat. No. 18620) as the light-emitting particle. For the sample solutions, phosphate buffers (including 0.05% Tween20) including ATTO633 at its concentration of 0 fM (with no dye), 10 fM, 100 fM, 1 pM, 10 pM, 100 pM, and 1 nM were prepared, respectively.

In the measurement in accordance with the inventive optical analysis technique, a single molecule fluorescence measuring apparatus MF20 (Olympus Corporation), equipped with the optical system of a confocal fluorescence microscope and a photon counting system was used as the optical analysis device, and time series light intensity data were acquired for the above-mentioned respective sample solutions in accordance with the manner explained in the above-mentioned "(1) Measurement of the light intensity of a sample solution". For the objective, a water immersion objective (40×, NA=1.15, WD=0.26) was used. In this connection, for the photodetector 16, a super high sensitive photodetector capable of detecting an arrival of a single photon was used, and thereby the light detection was the photon counting performed sequentially for a predetermined term in a manner that the number of photons arriving at the photodetector in every predetermined unit time (BIN TIME) was measured. Accordingly, the time series light intensity data is time series photon count data. Further, a 633 nm laser light was used for excitation light, and the detected light wavelength was set from 660 to 710 nm using a band pass filter. Measurement for 2 seconds was performed 3 times, where the moving speed of the position of the light detection region in the sample solution was set to 15 mm/second and BIN TIME was set to 10 μsec.

Figure 5A:
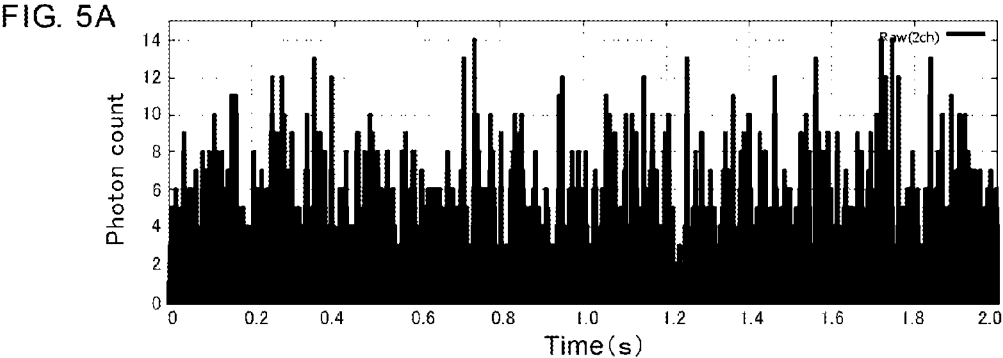
FIG. 5A is a diagram showing the whole time series photon count data measured in accordance with the inventive optical analysis technique.
Figure 5B:
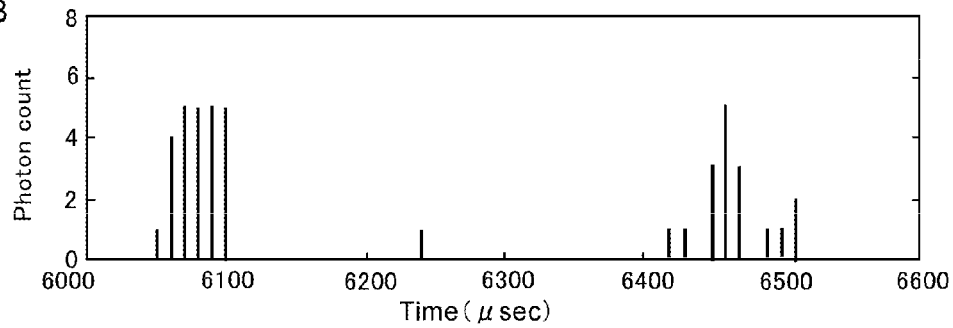
FIG. 5B is an enlarged diagram of several sections of time series photon count data, where various characteristic values computed for the sections referred to are also shown.

FIG. 5A shows an example of the whole time series photon count data obtained by a measurement for 2 seconds, and FIG. 5B shows an enlarged diagram of a part of the time series photon count data of the measurement for 2 seconds. After the above-mentioned measurement of light intensity, for the detection of a light signal of a light-emitting particle in the time series photon count data acquired for each sample solution, the whole region of the time series photon count data was divided into time sections having the width of 200 μsec. as illustrated in FIG. 5B, and in each of the time sections, as the characteristic value of light intensity indicating the presence or absence of light from a single light-emitting particle, the total value of photon counts, the center value of photon counts, the average value of photon counts, the standard deviation value of photon counts (SD value), the variance of photon counts, the entropy value of photon counts, the maximum value of photon counts and the number of particles computed from an autocorrelation function value of photon counts with a correlation time being set to 0 were computed. As the results, for example, as shown by FIG. 5B, in the sections in which it could be judged visually that a light signal of a light-emitting particle existed (Window #30, Window #32), the illustrated characteristic values were larger than those in the section (Window #31) in which it could be judged that no light signal of a light-emitting particle existed.

Figure 6:
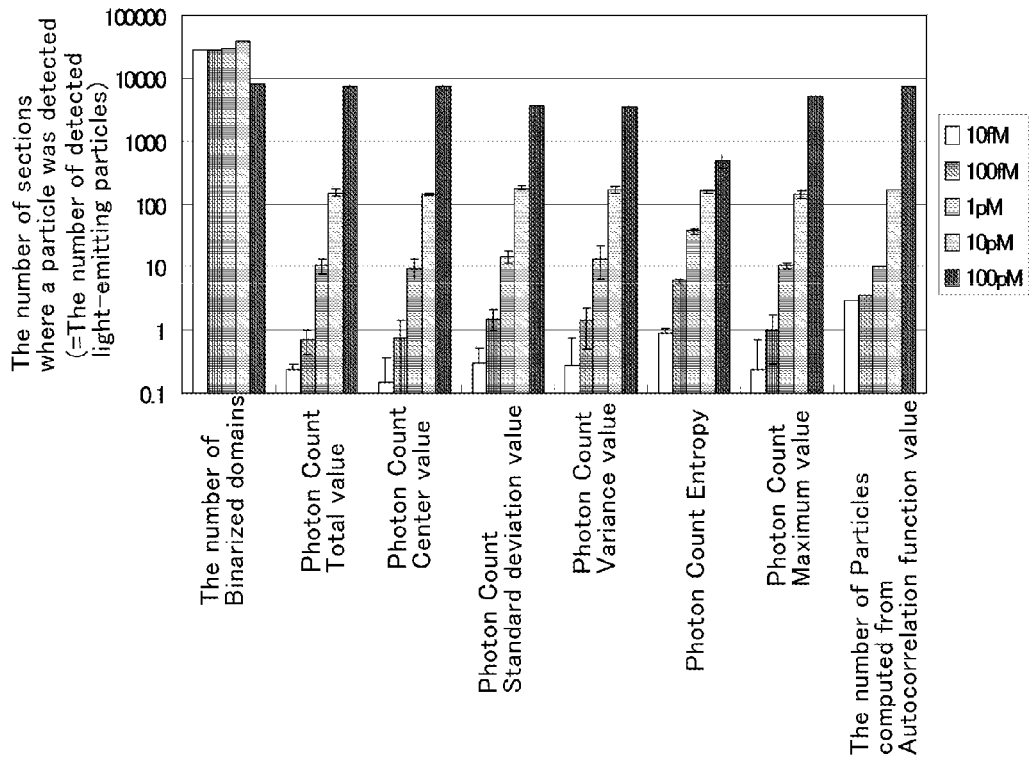
FIG. 6 shows the number of light-emitting particles detected individually in time series photon count data using the characteristic values computed in accordance with the present invention for the respective solutions containing light-emitting particles at a concentration of 10 fM-100 pM.

Thus, after computing the characteristic values of light intensity for every time section in the whole region of the time series photon count data, under the assumption that the light signal of one light-emitting particle existed in the time section in which each of the characteristic values exceeded beyond the corresponding predetermined threshold value, for each of the characteristic values, the number of the time sections in which the characteristic value exceeded beyond the predetermined threshold value was counted. FIG. 6 shows the number of the time sections having the respective characteristic values exceeding beyond the corresponding predetermined threshold values, for each of the above-mentioned solutions. The threshold value of each characteristic value was set as follows.

| | |
|---|---|
| Total value of photon counts | 100 counts |
| Center value of photon counts | 4.5 counts |
| Standard deviation value of photon counts | 3.5 counts |
| Variance value of photon counts | 12.5 counts |
| Entropy value of photon counts | 105 |
| Maximum value of photon counts | 13 counts |
| The number of Particles (Computed from Autocorrelation function value to computation) | 0.4 particles |

In this regard, for comparison, there are described also the number of the continuous time domains in which the photon count exceeded 2 in the time series photon count data (binarized domain number).

Referring to FIG. 6, each of the illustrated characteristic values increased with the increase of the light-emitting particle concentration in the sample solution. However, with respect to the number of particles computed from the autocorrelation function value of the photon counts with the correlation time being set to 0, no remarkable change was seen with light-emitting particle concentration of less than 1 pM. On the other hand, regarding the binarized domain number, no remarkable concentration dependency were obtained for the sample solutions used for the measurement. Thus, the above-mentioned results suggest that the light from a light-emitting particle is detected individually and its concentration can be determined by referring to a characteristic value of light intensity indicating the presence or absence of light from a single light-emitting particle computed for every time section of a predetermined width in the time series light intensity data obtained by measuring light in accordance with the present invention.

Figure 7:
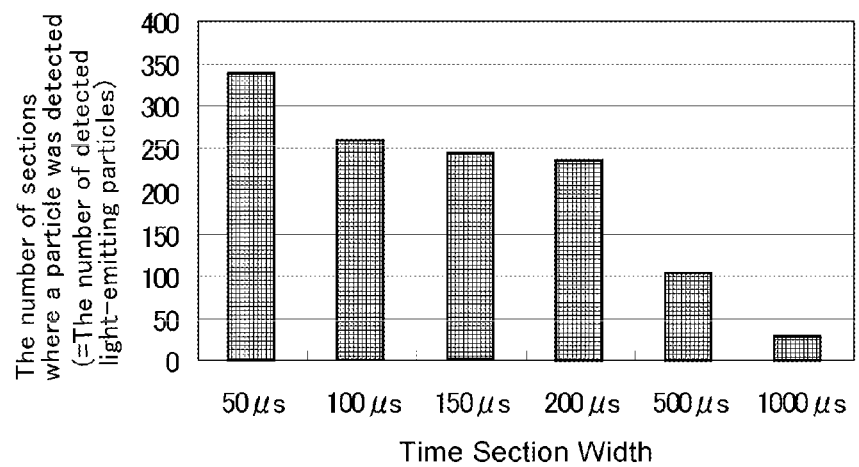
FIG. 7 is a diagram showing the relation between the predetermined width of the time section in the time series photon count data and the number of the sections in which the existence of a light-emitting particle was detected, in accordance with the inventive optical analysis technique.

Furthermore, in the above-mentioned time series photon count data, the influence of the width of the time section in computing a characteristic value on the detected number of the light-emitting particles was tested. FIG. 7 shows the detected number of the light-emitting particles (the number of the time sections where a characteristic value exceeded the predetermined threshold value) in changing the width of the time section in computing a characteristic value (the total value of photon counts) in the time series photon count data of the sample solution of the light-emitting particle concentration of 10 pM. Referring to the drawing, in the case that the time section width was 100 to 200 μsec., the detected number of the light-emitting particles was stabilized. On the other hand, when the time section width was less than 100 μsec., the detected number of particles increased apparently. Since the time required for a single light-emitting particle to pass through the light detection region linearly was computed as about 74 μsec. in the condition of the measurement of this experimental example, it is considered that the number of times that one light-emitting particle was detected over two or more time sections was reduced by making the time section width longer than the time required for a single light-emitting particle to pass through the light detection region linearly. Moreover, in the above results, when the time section width exceeded beyond 200 μsec., the detected number of particles was reduced apparently. This is considered to be because making the time section width longer increases the number of the time sections in which light signals of two or more light-emitting particles exist. Actually, in the above-mentioned solution condition and device condition, the upper limit of high of the predetermined width of the time section, computed using the expression (2d) with the allowable error being about 5%, was about 200 μsec. (the radius Wo of the light detection region was set to be ~1 μm.). These results suggest that one light-emitting particle can be made to correspond to one time section by setting the width of the time section substantially longer than a time width required for an interval from a time of one light-emitting particle's entering into the light detection region to a time of its exiting therefrom, and also substantially shorter than a time width from a time of one light-emitting particle's entering into the light detection region to a time of a different light-emitting particle's entering into the light detection region.

Thus, it has been shown that, according to the inventive optical analysis technique, the number density or concentration of a light-emitting particle can be determined in the concentration range lower than the limit of the number density or concentration measurable by conventional methods using fluorescence intensity. Further, while the lower limit of particle concentration measurable in optical analysis techniques, such as FCS, FIDA, and PCH, including statistical procedures, e.g. calculation of fluorescence intensity fluctuation was about 1 nM, the lower limit of the particle concentration measurable in the present embodiment was ~10 fM, and accordingly, it has been also shown that, according to the present invention, the measurement is possible for a particle in the range of a concentration significantly lower than the case of the optical analysis techniques such as FCS, FIDA and PCH.

We claim:

1. An optical analysis device which detects light from a light-emitting particle dispersed and moving at random in a sample solution by using an optical system of a confocal microscope or a multiphoton microscope, wherein the device comprises:
   a light detection region moving mechanism moving a position of a light detection region of the optical system in the sample solution;
   a light detector detecting light from the light detection region; and
   a signal processor generating time series light intensity data of the light from the light detection region detected with the light detector during moving the position of the light detection region in the sample solution, and detects individually a light signal from each light-emitting particle in the time series light intensity data;
   wherein the signal processor computes a characteristic value of light intensity indicating a presence or an absence of the light from a single light-emitting particle in every time section of a predetermined width in the time series light intensity data, and detects individually a light signal from each light-emitting particle, using the characteristic value.

2. The device of claim 1, wherein the signal processor counts the number of the light-emitting particle(s) detected during the moving of the position of the light detection region by counting the number of the time section(s) of the predetermined width having a light signal from a light-emitting particle.

3. The device of claim 1, wherein the light detector detects the light from the light detection region by photon counting, and the time series light intensity data is time series photon count data.

4. The device of claim 3, wherein the characteristic value of the light intensity is a value selected from a group of a total value of photon counts, a center value of photon counts, an average value of photon counts, a standard deviation of photon counts, a variance of photon counts, an entropy of photon counts, a maximum value of photon counts and the number of particles computed from an autocorrelation function value of photon counts with a correlation time being set to 0, in the time section of the predetermined width.

5. The device of claim 1, wherein the light detection region moving mechanism moves the position of the light detection region at a velocity faster than a diffusional moving velocity of the light-emitting particle.

6. The device of claim 1, wherein the characteristic value of the light intensity in the time section of the predetermined width in which light from a single light-emitting particle exists is larger than the characteristic value of the light intensity in the time section of the predetermined width in which no light from a single light-emitting particle exist, and it is judged that the light signal from the light-emitting particle exists in the time section of the predetermined width when the characteristic value of the light intensity is larger than a predetermined threshold value.

7. The device of claim 1, wherein the predetermined width is set to be substantially longer than a time width required for an interval from a time of one light-emitting particle's entering into the light detection region to a time of the one light-emitting particle's exiting therefrom, and also substantially shorter than a time width from a time of one light-emitting particle's entering into the light detection region to a time of a different light-emitting particle's entering into the light detection region.

8. The device of claim 1, wherein the signal processor determines a number density or a concentration of the light-emitting particle in the sample solution based on the number of the detected light-emitting particle(s).

9. An optical analysis method of detecting light from a light-emitting particle dispersed and moving at random in a sample solution by using an optical system of a confocal microscope or a multiphoton microscope, said method comprising steps of:
- moving a position of a light detection region of the optical system in the sample solution;
- detecting light from the light detection region while moving the position of the light detection region in the sample solution and generating time series light intensity data;
- computing a characteristic value of light intensity indicating a presence or an absence of the light from a single light-emitting particle in every time section of a predetermined width in the time series light intensity data; and
- detecting individually a light signal from each light-emitting particle, using the characteristic value of light intensity in each of the time section(s) of the predetermined width.

10. The method of claim 9, further comprising a step of counting the number of the light-emitting particle(s) detected during the moving of the position of the light detection region by counting the number of the time sections of the predetermined width having a light signal from a light-emitting particle.

11. The method of claim 9, in that, in the step of detecting light from the light detection region and generating time series light intensity data, the light from the light detection region is detected by photon counting, and the time series light intensity data is time series photon count data.

12. The method of claim 11, wherein the characteristic value of the light intensity is a value selected from a group of a total value of photon counts, a center value of photon counts, an average value of photon counts, a standard deviation of photon counts, a variance of photon counts, an entropy of photon counts, a maximum value of photon counts and a the number of particles computed from an autocorrelation function value of photon counts with a correlation time being set to 0, in the time section of the predetermined width.

13. The method of claim 9, wherein, in the step of moving the position of the light detection region, the position of the light detection region is moved at a velocity faster than a diffusional moving velocity of the light-emitting particle.

14. The method of claim 9, wherein the characteristic value of the light intensity in the time section of the predetermined width in which light from a single light-emitting particle exists is larger than the characteristic value of the light intensity in the time section of the predetermined width in which no light from a single light-emitting particle exist, and it is judged that the light signal from the light-emitting particle exists in the time section of the predetermined width when the characteristic value of the light intensity is larger than a predetermined threshold value.

15. The method of claim 9, wherein the predetermined width is set to be substantially longer than a time width required for an interval from a time of one light-emitting particle's entering into the light detection region to a time of the one light-emitting particle's exiting therefrom, and also substantially shorter than a time width from a time of one light-emitting particle's entering into the light detection region to a time of a different light-emitting particle's entering into the light detection region.

16. The method of claim 9, further comprising a step of determining a number density or a concentration of the light-emitting particle in the sample solution based on the number of the detected light-emitting particle(s).

17. A computer readable storage device having a computer program product including programmed instructions for optical analysis for detecting light from a light-emitting particle dispersed and moving at random in a sample solution by using an optical system of a confocal microscope or a multiphoton microscope, said programmed instructions causing a computer to perform steps of:
- moving a position of a light detection region of the optical system in the sample solution;
- detecting light from the light detection region while moving the position of the light detection region in the sample solution and generating time series light intensity data;
- computing a characteristic value of light intensity indicating a presence or an absence of the light from a single light-emitting particle in every time section of a predetermined width in the time series light intensity data; and
- detecting individually a light signal from each light-emitting particle, using the characteristic value of light intensity in each of the time sections of the predetermined width.

18. The computer readable storage device of claim 17, further comprising a step of counting the number of the light-emitting particle(s) detected during the moving of the position of the light detection region by counting the number of the time section(s) of the predetermined width having a light signal from a light-emitting particle.

19. The computer readable storage device of claim 17, wherein, in the step of detecting light from the light detection region and generating time series light intensity data, the light from the light detection region is detected by photon counting, and the time series light intensity data is time series photon count data.

20. The computer readable storage device of claim 19, wherein the characteristic value of the light intensity is a value selected from a group of a total value of photon counts, a center value of photon counts, an average value of the photon counts, a standard deviation of photon counts, a variance of photon counts, an entropy of photon counts, a maximum value of photon counts and the number of particles computed from an autocorrelation function value of photon counts with a correlation time being set to 0, in the time section of the predetermined width.

21. The computer readable storage device of claim 17, wherein, in the step of moving a position of a light detection region of the optical system, the position of the light detection region is moved at a velocity faster than a diffusional moving velocity of the light-emitting particle.

22. The computer readable storage device of claim 17, wherein the characteristic value of the light intensity in the time section of the predetermined width in which light from a single light-emitting particle exists is larger than the characteristic value of the light intensity in the time section of the predetermined width in which no light from a single light-emitting particle exist, and it is judged that the light signal from the light-emitting particle exists in the time section of the predetermined width when the characteristic value of the light intensity is larger than a predetermined threshold value.

23. The computer readable storage device of claim 17, wherein the predetermined width is set to be substantially longer than a time width required for an interval from a time of one light-emitting particle's entering into the light detection region to a time of the one light-emitting particle's exiting therefrom, and also substantially shorter than a time width from a time of one light-emitting particle's entering into the light detection region to a time of a different light-emitting particle's entering into the light detection region.

24. The computer readable storage device of claim 17, further comprising a step of determining a number density or a concentration of the light-emitting particle in the sample solution based on the number of the detected light-emitting particle(s).

\* \* \* \* \*